US012766072B2

(12) United States Patent
Davis

(10) Patent No.: US 12,766,072 B2
(45) Date of Patent: Oct. 20, 2026

(54) EXTENDER FOR A PERCUSSION MASSAGE DEVICE

(71) Applicant: Robert Davis, Carlsbad, CA (US)

(72) Inventor: Robert Davis, Carlsbad, CA (US)

( * ) Notice: Subject to any disclaimer, the term of this patent is extended or adjusted under 35 U.S.C. 154(b) by 410 days.

(21) Appl. No.: 17/383,099

(22) Filed: Jul. 22, 2021

(65) Prior Publication Data

US 2023/0027314 A1 Jan. 26, 2023

(51) Int. Cl.

| | |
|---|---|
| ***A61H 37/00*** | (2006.01) |
| ***A61F 4/00*** | (2006.01) |
| ***A61H 23/00*** | (2006.01) |
| ***B25G 1/04*** | (2006.01) |
| ***B25G 3/20*** | (2006.01) |
| ***B25G 3/38*** | (2006.01) |

(52) U.S. Cl.

CPC ............... *A61H 37/00* (2013.01); *A61F 4/00* (2013.01); *A61H 23/006* (2013.01); *B25G 1/04* (2013.01); *B25G 3/20* (2013.01); *B25G 3/38* (2013.01); *A61H 2201/0153* (2013.01); *A61H 2201/0157* (2013.01); *A61H 2201/0161* (2013.01); *A61H 2201/0192* (2013.01)

(58) Field of Classification Search

CPC ... B25G 1/04; B25G 3/38; B25G 3/20; A61H 2201/0192; A61H 2201/0153; A61H 23/006; A61H 37/00; A61H 2201/0161; A61F 4/00

See application file for complete search history.

(56) References Cited

U.S. PATENT DOCUMENTS

| | | | | | | |
|---|---|---|---|---|---|---|
| 1,884,161 | A | * | 10/1932 | Orr | A61H 7/002 | 601/89 |
| 2,568,654 | A | * | 9/1951 | Neptune | A61H 3/02 | 135/69 |
| 2,741,255 | A | * | 4/1956 | Neptune | A61H 3/02 | 403/374.5 |
| 2,817,348 | A | * | 12/1957 | Holliday, Jr. | A61H 3/02 | 135/69 |
| 3,768,495 | A | * | 10/1973 | Smith | A61H 3/02 | 135/69 |
| 4,196,742 | A | * | 4/1980 | Owen, Jr. | A61H 3/0288 | 280/821 |
| 4,508,364 | A | * | 4/1985 | Joseph | A63C 11/22 | 280/821 |
| D317,204 | S | * | 5/1991 | Henneseey | D24/211 | |
| 5,890,259 | A | * | 4/1999 | Sarac | B25G 1/102 | 16/901 |
| 6,026,535 | A | * | 2/2000 | Lankowski | A45D 34/04 | 15/210.1 |
| 6,032,321 | A | * | 3/2000 | Shirey | B25G 1/06 | 15/144.4 |
| 6,101,657 | A | * | 8/2000 | Hamilton | B25G 1/04 | 81/177.1 |

(Continued)

*Primary Examiner* — Jeffrey O'Brien

(57) ABSTRACT

An extender for a massage device handle has an adjustable and pivotal sleeve to be removably attached to different sized massage device handles via a hinge assembly. A first longitudinal extender section is removably attached to the hinge assembly. A first laterally extending handle is removably attached to the first longitudinal extender section. The first longitudinal extender section has one end adapted to removably receive another extender section to extend the length of the extender.

10 Claims, 7 Drawing Sheets

(56) References Cited

U.S. PATENT DOCUMENTS

| | | | | | |
|---|---|---|---|---|---|
| 6,151,789 | A * | 11/2000 | Raab | G01B 21/047 33/503 |
| 6,851,438 | B2 * | 2/2005 | Battiston | A61H 3/02 135/69 |
| 8,151,828 | B2 * | 4/2012 | Parton | F16L 55/1705 137/15.01 |
| 8,257,412 | B1 * | 9/2012 | Skoog | A61N 5/06 606/19 |
| 8,382,727 | B1 * | 2/2013 | Martin | A45D 34/041 604/289 |
| D691,731 | S * | 10/2013 | Grippo | A61H 7/003 D24/214 |
| 9,168,196 | B2 * | 10/2015 | Dagan | A61H 39/04 |
| 9,168,198 | B2 | 10/2015 | Dagan | |
| 9,364,136 | B2 * | 6/2016 | Devir | B25G 1/04 |
| 9,532,918 | B1 * | 1/2017 | Louis | A61H 7/003 |
| 9,561,150 | B2 * | 2/2017 | Dickerson, II | A61H 3/02 |
| 9,604,376 | B2 * | 3/2017 | Sacks | B25G 3/02 |
| 10,357,425 | B2 * | 7/2019 | Wersland | A61H 1/008 |
| 10,426,689 | B2 * | 10/2019 | Weber | A61H 3/0277 |
| D872,869 | S * | 1/2020 | Lu | D24/215 |
| 10,548,808 | B2 * | 2/2020 | Leier | A61H 15/0092 |
| D884,915 | S * | 5/2020 | Wersland | D24/115 |
| 10,820,671 | B1 * | 11/2020 | Chen | B25G 3/12 |
| 11,179,842 | B2 * | 11/2021 | Newman | B25G 3/26 |
| D947,399 | S * | 3/2022 | Mao | D24/214 |
| D949,391 | S * | 4/2022 | Wersland | D24/115 |
| D950,750 | S * | 5/2022 | Bernstein | D24/215 |
| 11,452,670 | B2 * | 9/2022 | Wersland | A61H 23/0254 |
| 11,752,614 | B2 * | 9/2023 | Cariello | B25G 1/04 16/429 |
| 11,974,956 | B2 * | 5/2024 | Lawrie | A61H 23/006 |
| 12,377,530 | B2 * | 8/2025 | Gurule | A46B 17/02 |
| 2009/0159487 | A1 * | 6/2009 | Tacoma | B25J 1/04 15/210.1 |
| 2011/0294634 | A1 * | 12/2011 | Bua | A61H 1/0281 482/139 |
| 2013/0066245 | A1 * | 3/2013 | Dagan | A61H 7/003 601/118 |
| 2015/0374576 | A1 * | 12/2015 | Dagan | A61H 7/003 601/119 |
| 2016/0206051 | A1 * | 7/2016 | Minson | A44B 11/04 |
| 2017/0113029 | A1 * | 4/2017 | Hernandez | A61M 35/003 |
| 2017/0334081 | A1 * | 11/2017 | Dryfhout | B26B 21/44 |
| 2021/0161759 | A1 * | 6/2021 | Minkus | A61H 37/00 |
| 2021/0244609 | A1 * | 8/2021 | Lee | A61H 23/006 |
| 2021/0291352 | A1 * | 9/2021 | Celis | B65G 7/12 |
| 2021/0361519 | A1 * | 11/2021 | Hagy | A61H 7/005 |
| 2022/0104997 | A1 * | 4/2022 | Lawrie | A61H 37/00 |
| 2022/0117841 | A1 * | 4/2022 | Tellam | A61H 37/00 |
| 2024/0130928 | A1 * | 4/2024 | Glassman | A61H 23/006 |

* cited by examiner

EXTENDER FOR A PERCUSSION MASSAGE DEVICE

BACKGROUND OF THE INVENTION

Field of the Invention

Various types of personal massage equipment are designed to enable an individual to apply a massage therapy on another individual. For example, a percussion massage device has a small handle to be held by a masseuse who uses the device to treat a massage patient. A handle's shape plays an important role in enabling the user to apply the massage therapy. As an example, a handle can be extended to enable a user to reach otherwise difficult to reach places. An extended handle is particularly useful when the user wants to apply the massage therapy to him or herself instead of another person.

The presently disclosed device relates to extending the handle of a massage device. Particularly, the handles of massage devices can be extended to enable the user to apply the massage therapy to him or herself without having to rely on another person. This is critical when no one else is around. The presently disclosed device is also designed with the handicapped in mind. Whether a user is in a wheel chair or ambulatory in a bed and is unable to reach their legs, calves and feet, the present device can be made instantly longer by adding in a first embodiment sections or using the telescoping mechanism of a second embodiment.

Problem to be Solved

The difficulty of a self-induced therapy with a massage device is that the handles of the massage devices are only long enough to hold in one or two hands, and do not extend far enough for an individual to precisely target critical parts of their body. For example, a large section of a person's back is inaccessible during a self-induced therapy due to the inability of the human arm to control a massage gun around the upper, mid, and lower sections of the back. Even the strongest and most flexible athletes have challenges reaching these areas. Not only are these areas of the body extraordinarily difficult to reach with precision, but it is even more difficult to apply a constant pressure needed to satisfy the therapeutic need. Even where these limitations could be overcome by a very determined user, the user is indeed strained in attempting to do so and the therapy has little-to-no effect because the user is not relaxed. By involving targeted muscle groups in carrying out the therapeutic process, the user is unable to realize the full effect of any therapy applied to those muscle groups.

Description of Prior Art

Existing prior art includes many different types of handheld percussion massage gun devices, none of which were found to include an extendable handle. Alternatively, some non-percussion style massage devices were found to reach around the human back. For example, U.S. Pat. No. 9,168,196 is a solid frame handle that enables a user to target hard-to-reach areas of their back. However, this handle is not able to be used independently by the user. Use of this handle requires a wall to provide the necessary pressure on the back. It also requires that the user stand in an upright position, rather than in a relaxed position such as lying on a bed. The user must exert substantial effort by squatting or raising their entire torso up and down to effectuate the massage therapy. Not only is this handle limited to reaching only areas on the back, it is not compatible with other handheld massage devices such as a percussion massage gun.

A person having ordinary skill in the art is any user who senses tension in any of the various muscle groups and wishes to apply massage therapy using a percussion massage gun. When applying treatment on another person, that person could be either a masseuse, or a family member or friend. With self-induced therapy, however, the person having ordinary skill in the art is anyone wishing to use a massage device on themselves.

The present extender enables the user to apply massage therapy using various massage devices on his or herself and with minimal effort. The user can achieve a relaxed position during the self-induced therapy. The extender is not limited to any particular type of massage device (e.g. percussion massage gun); it is compatible with virtually any massage device that has a handle. Although prior art was discovered to include a percussion or tapping massage gun, such as U.S. Pat. No. 10,357,425, no prior art found features any sort of inter-functionality with an extendable handle attachment, and a unique universal fully adjustable massage gun receiving holder that can also be angled to create better leverage on a trigger actuated by the user. Patent No. 10,357,425 is not designed to be attached to a separate extendable handle, the user merely grips the built-in handle and applies therapy within arm's length. The arm's length limitation prevents self-induced therapy to numerous muscles in their natural, relaxed state. The very muscles used to hold the heavy massage gun are the same muscles the user is trying to relax. The extender can selectively extend a massage device handle to various lengths and enables the user to angle the massage device at various angles to reach hard-to-reach muscles in a number of ways. While the user is in bed, the extender can be placed on the bed as the user slides the extender effortlessly to reach areas of the lower body allowing the bed to support the weight of the unit and not the user. Because of the adjustable nature in the length of the extender, greater leverage is achieved with significant decrease in effort. The extender increases the ability to apply greater pressure to the targeted area of the body, allowing the muscles to relax more. For example, if the extender with the massage device is resting on the trapezius muscle on the user's neck, an arm can be draped over the handle to take advantage of the weight of the arm and gravity while the user relaxes and lets the massager do all the work.

Statement of the Objects of the Invention

The object of the presently defined device is to extend the length of a massage device handle to enable the user to allow the massager to reach areas with greater leverage on the intended area, which areas are otherwise inaccessible to someone using a massage gun on themselves without the extender.

SUMMARY OF THE INVENTION

The presently defined extender for a massage device provides the user with the ability to apply self-induced massage therapy by extending the handle of the massage device. Areas of the user's body that are normally inaccessible become accessible with the extender. A sleeve or strap firmly wraps around the handle of the massage device, firmly and removably gripping the handle. The sleeve is attached to a rotating locking member which connects the sleeve to an extendable handle. The rotating locking member is configured to disengage at one angle and reengage at a different angle. The angle of the locking member varies and enables the extendable handle to pivot at various angles with the massage device handle. The extendable handle can be configured with one or more extensions or with a protracting and extending sliding adjustable mechanism similar to a tripod telescoping extending leg. The handle is extendable to enable the user to reach the more distant and difficult areas of the user's body, and to increase one's leverage such that the user needs to apply less strength.

DESCRIPTION OF THE ILLUSTRATED EMBODIMENTS

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

DESCRIPTION

Figure 1:
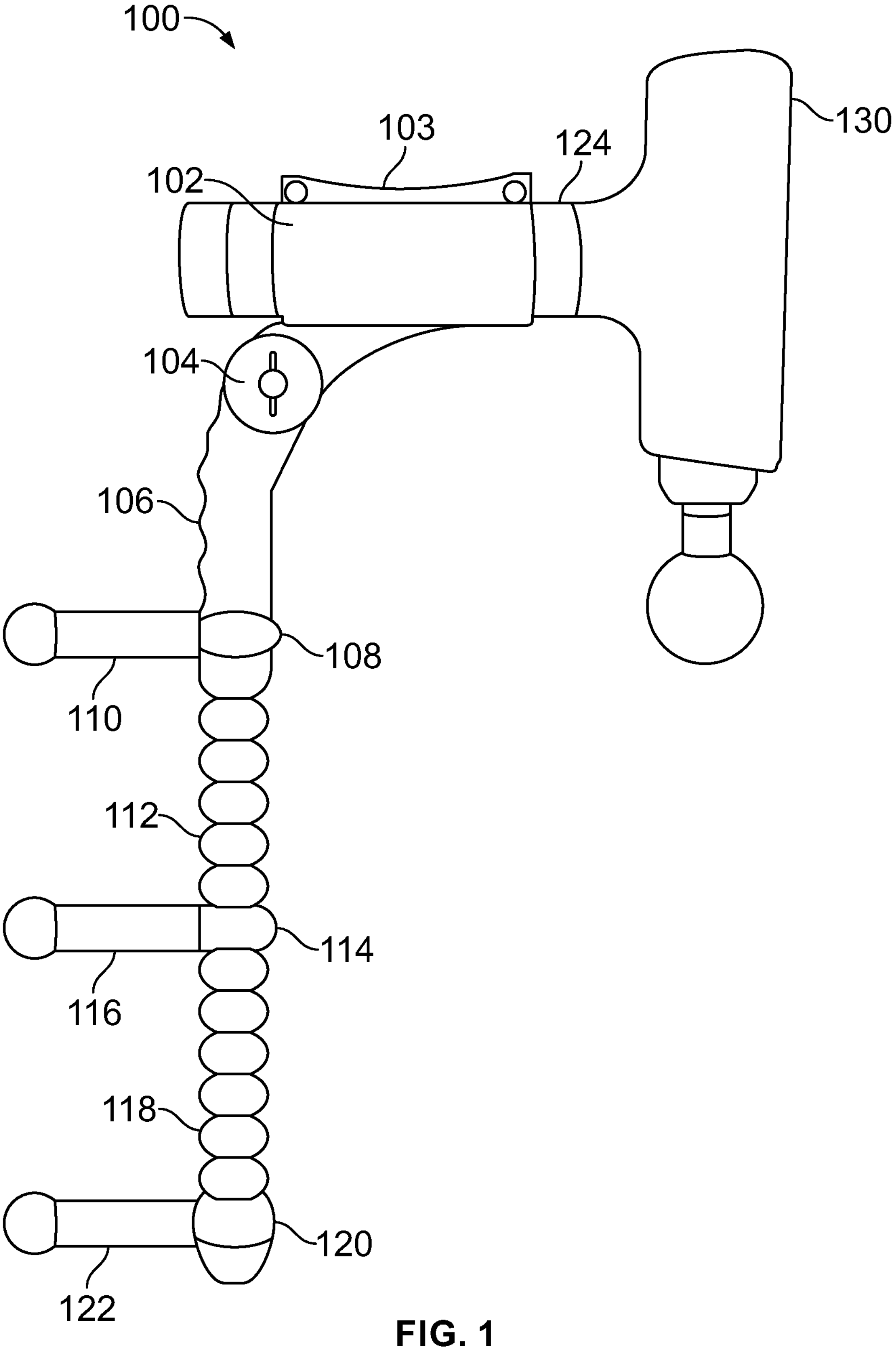
FIG. 1 shows a side view of a first embodiment of an extender assembly for a massage device.
Figure 2:
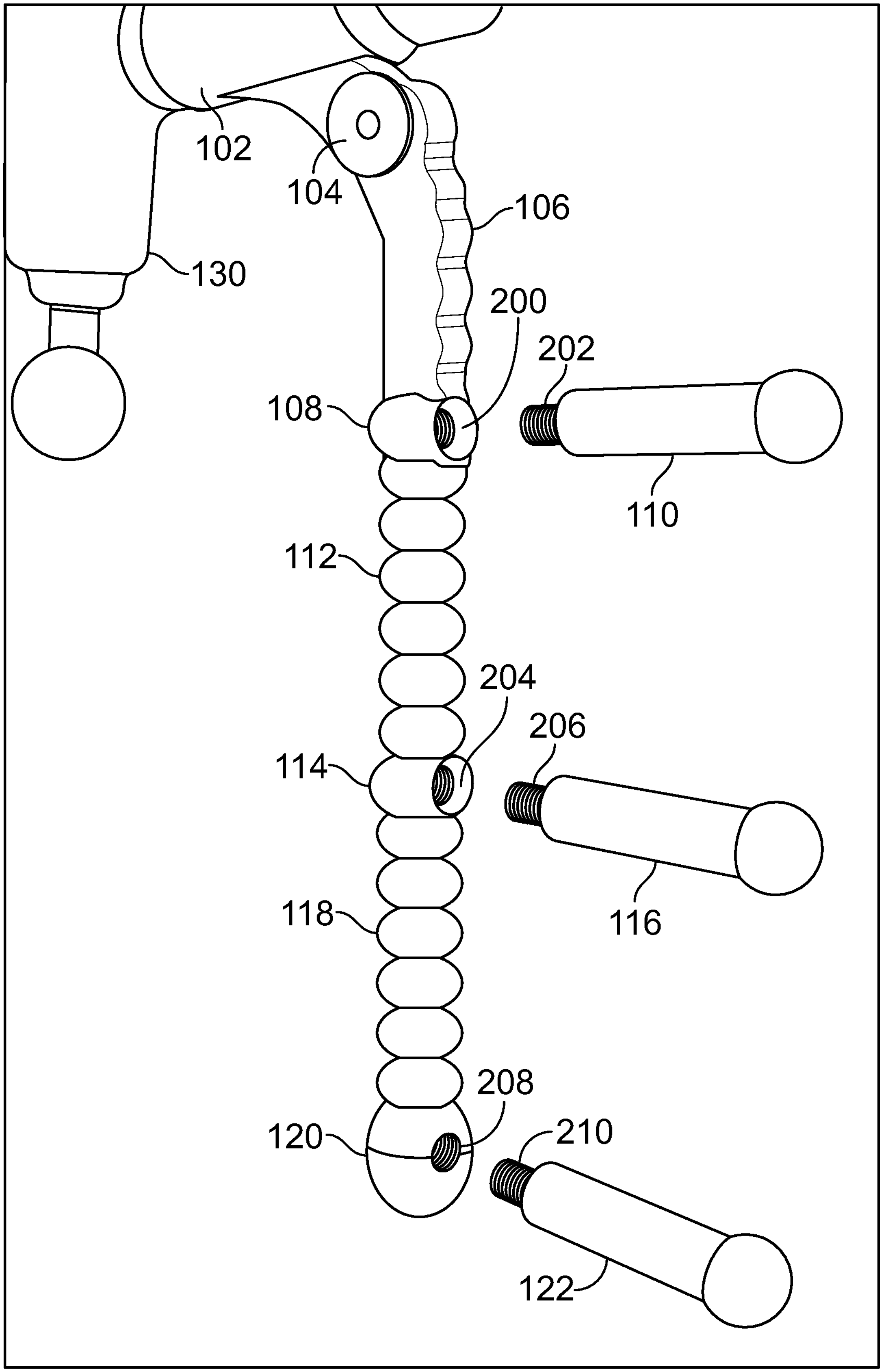
FIG. 2 is a partial exploded view of the embodiment of FIG. 1 of an extender assembly and the thread configuration of joint sections with intersecting handles.
Figure 3:
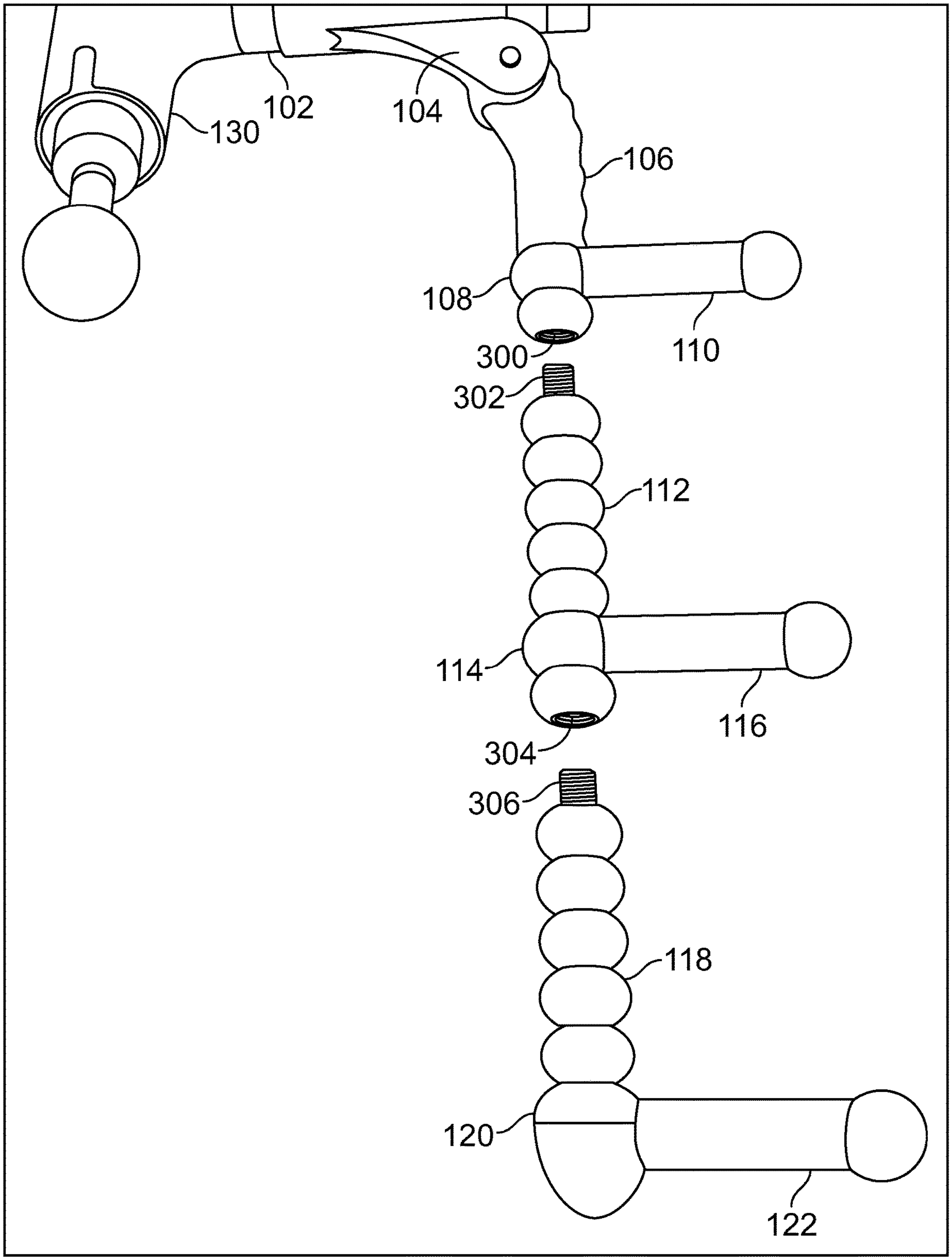
FIG. 3 is a partial exploded view of the embodiment of FIGS. 1 and 2 of an extender assembly and the thread configuration of joint sections with extender handles.

Referring to the first embodiment of the extender assembly 100 illustrated in FIGS. 1 to 3, the sleeve 102 provides for connection of extender assembly 100 to a handle 124 of percussion massage device 130. The sleeve 102 may completely or substantially envelop handle 124. An adjustable fastener mechanism 103 allows sleeve 102 to be tightened and loosened around handle 124. The extender sleeve 102 may also comprise other systems that are known in the art to secure the massage device to the extender assembly, such as a sleeve using a strap and a hook and loop fastener system, such as illustrated in the embodiment of FIGS. 4-7.

Attached to the sleeve 102 is a pivotal locking member 104 that adjustably connects the sleeve 102 to the top portion of first extender handle 106. The locking member 104 is adjustable to achieve a spectrum of user defined angles between the orientations of the sleeve 102 relative to the first extender handle 106.

The first extender handle 106 is permanently fixed to the locking member 104. Attached to a bottom portion of the first extender handle 106 is a first joint section 108. The first joint section 108 has a female thread 200 (FIG. 2) that removably receives a first perpendicular intersecting handle 110 having a male thread 202. The first joint section 108 has a female thread 300 (FIG. 3) that removably receives a second extender handle 112 having a male thread 302.

Referring to FIG. 2, the second extender handle 112 is removably connected to the first extender handle 106. Attached to the second extender handle 112 is a second joint section 114 that is structured the same as joint section 108. The second joint section 114 has a female thread 204 that removably receives a second intersecting handle 116 having a male thread 206. The first joint section has a female thread 304 (FIG. 3) that removably receives a third extender handle 118 having a male thread 306.

The third extender handle 118 is removably connected to the second extender handle 112. Attached to the third extender handle 118 is a third joint section 120 (FIG. 3). The third joint section 120, similar to joint section 108, includes a female thread 208 (FIG. 2) that removably receives the third intersecting handle 122 having a male thread 210. The third joint section 120 may be the final joint section necessary to achieve the desired length. If additional extender sections are desired, a third joint section 120 having a second female thread will be used to removably receive a fourth extender handle. This pattern continues until the desired length for the extender is achieved.

The first extender handle 106, second extender handle 112, and third extender handle 118 may comprise either a shaft or bead structure. A grip-like structure may also be used as seen on the first extender handle 106 (FIG. 1).

The user holds the first extender handle 106 and screws the first intersecting handle 110 into the first joint section 108. Next, the user screws the second extender handle 112 into the first joint section 108. The user then screws the second intersecting handle 116 into the second joint section 114. Finally, the user screws the third extender handle 118 into the second joint section 114. The user then screws the third intersecting handle 122 into the third joint section 120. This completes the assembly of an extender having three sections.

Figure 4:
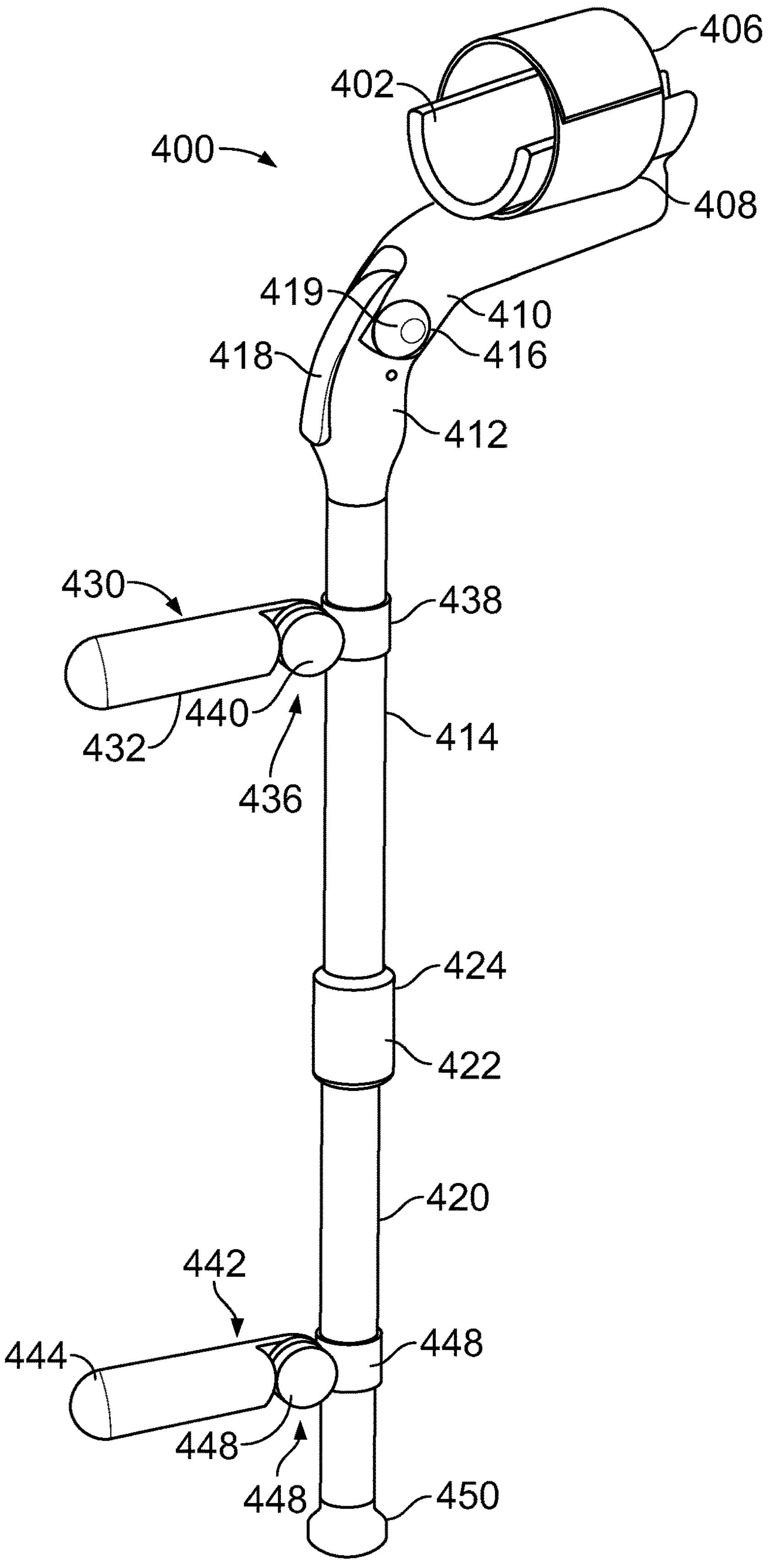
FIG. 4 is a perspective view of a second embodiment of the extender assembly for a massage device.
Figure 5:
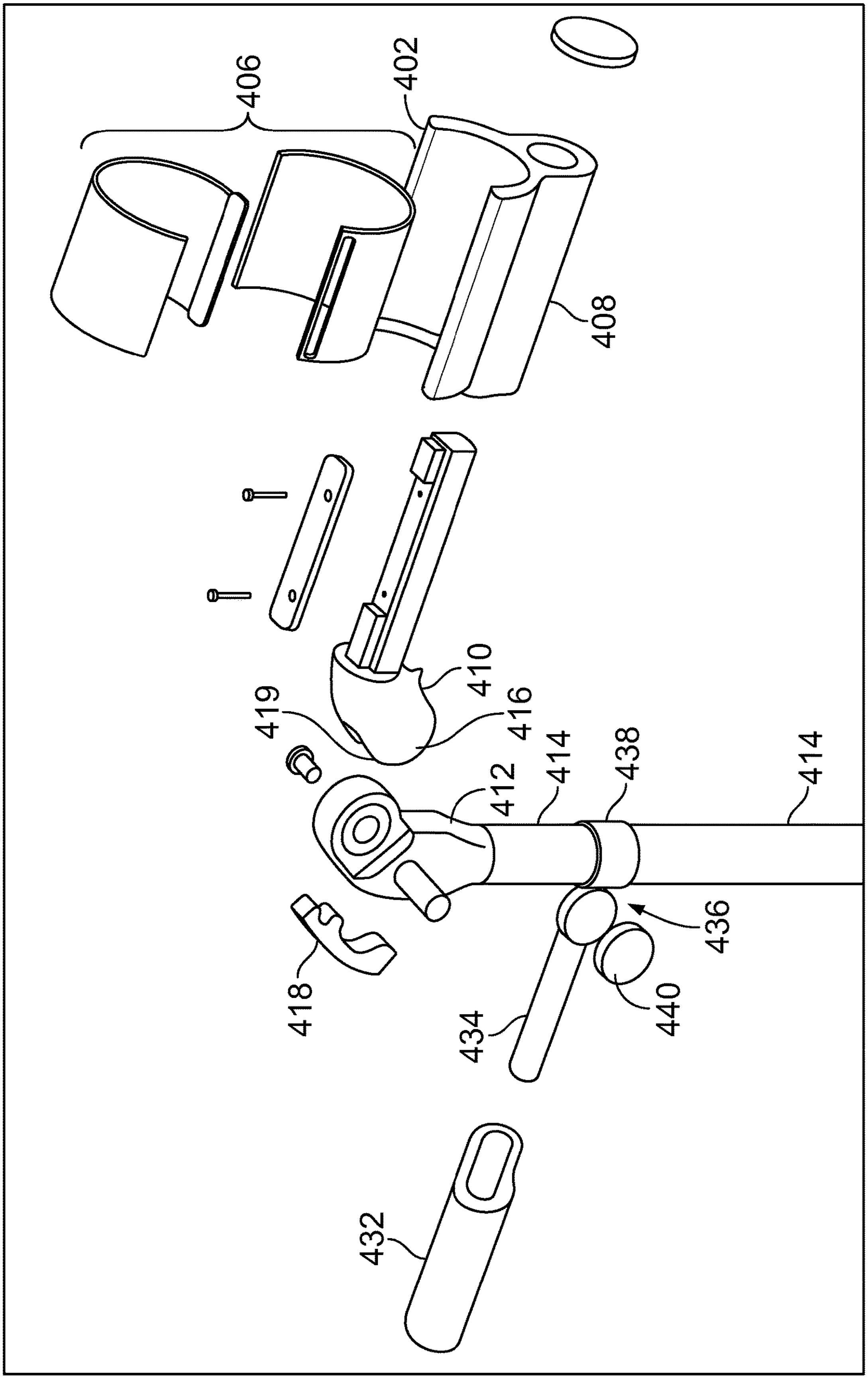
FIG. 5 is an exploded perspective view of the upper portion of the embodiment of the extender assembly shown in FIG. 4.
Figure 6A:
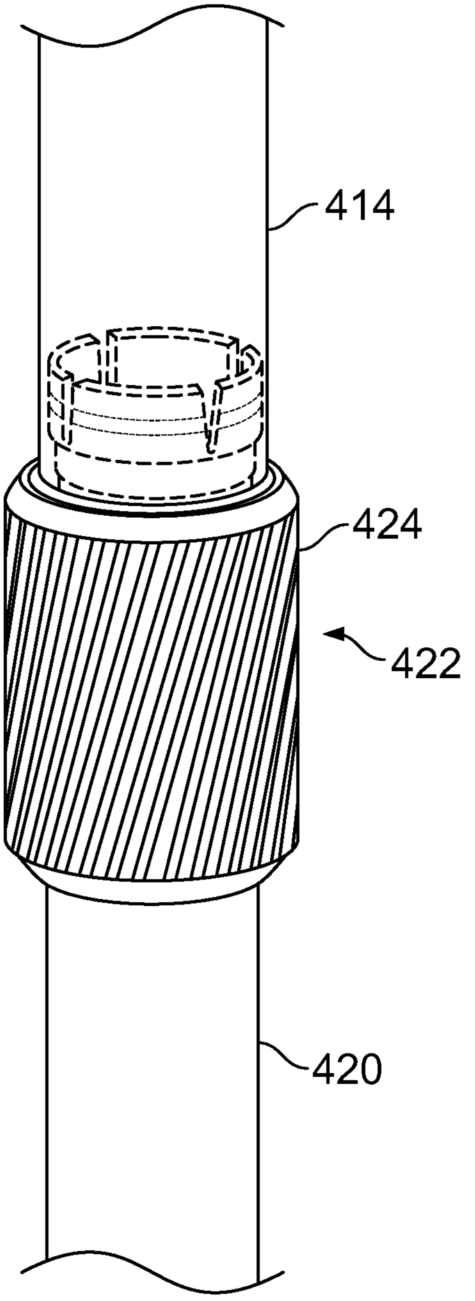
FIG. 6A is a detail perspective view of the telescopic mechanism of the embodiment of the extender assembly shown in FIG. 4.
Figure 6B:
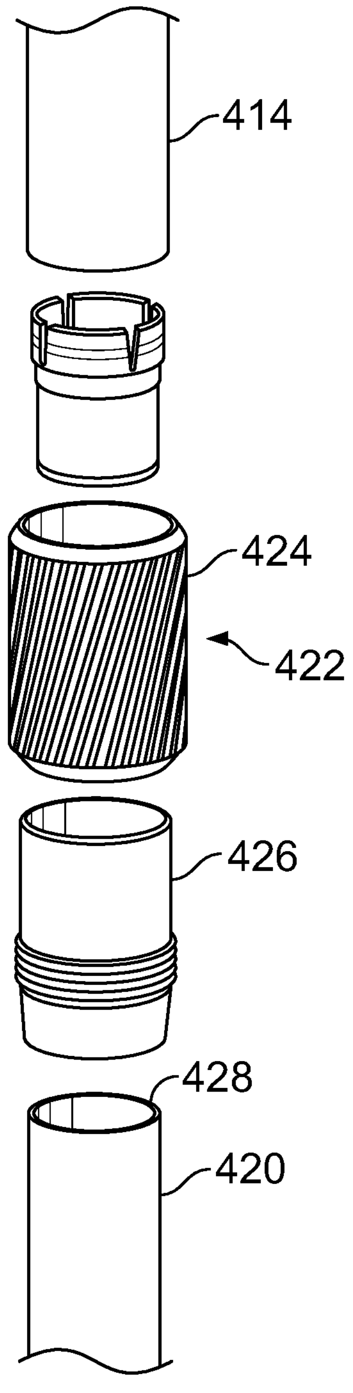
FIG. 6B is an exploded view of the telescopic mechanism of FIG. 6A.
Figure 7:
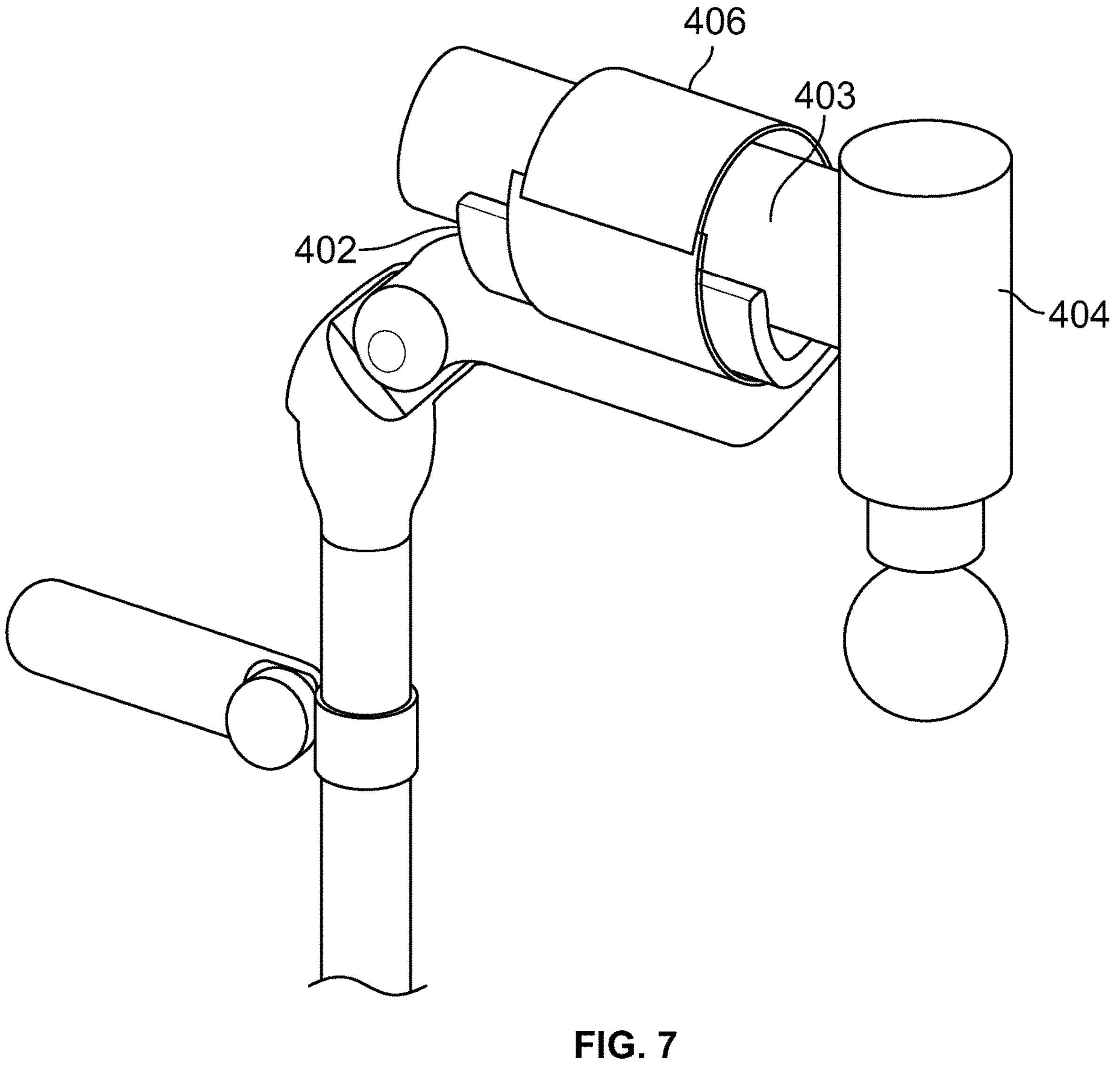
FIG. 7 is a perspective view of the extender mechanism embodiment of FIG. 4 supporting a percussion massage device.

A second embodiment of the presently disclosed extender assembly for a percussion massage device is illustrated in FIGS. 4-7. Referring first to FIG. 4, the extender assembly 400 comprises a semicircular cradle 402 adapted to support a circular housing of percussion massage device 404 (FIG. 7). A hook and loop fastener flexible strap assembly 406 extends through opposed slots 408 in cradle 402 to secure massage device 404 to cradle 402, as seen in FIG. 7.

a. A curved flange 410 extends outward and downward from cradle 402, and flange 410 is pivotally connected to an upper connecting portion 412 of first extender shaft 414 by a hinge assembly 416. The hinge assembly provides one hundred thirty five degree rotation between cradle 402 and first extender shaft 414. Trigger 418 is pivotally operable to unlock the hinge and enable rotation of cradle 402 relative to first extender shaft 414. Visual gradation indicia 419 on hinge assembly 416 allow the user to control the position of cradle 402.

b. In the illustrated embodiment of FIGS. 4-7, first extender shaft 414 is hollow, and a second extender shaft 420 is telescopically moveable in the hollow portion of first extender shaft 414 to vary the length of extender assembly 400. An extension ring 422 having a manual gripping surface 424 allows tightening and loosening of second extender shaft 420 relative to first extender shaft 414, allowing the expansion or retraction of extender assembly 400.

c. The gripping surface 424 of extension ring 422 is part of a telescoping locking mechanism well known in the art and is illustrated in detail in FIGS. 6A and 6B. A sleeve is installed over a first upper portion of the first extender shaft 414. The manual gripping surface 424 is installed over the top of the sleeve and envelops the first upper portion. Compression fitting 426 is installed over the second upper portion 428 of second extender shaft 420. The manual gripping surface 424 is attached over the top of compression fitting 426 and screws into the compression fitting 426.

First horizontal handle 430 extends laterally outward from first extender shaft 414. Handle 430 comprises a soft material grip 432 (FIG. 5) surrounding a solid shaft 434. One end of shaft 434 includes a gripping device 436 having a gripping band 438 extending around the outer circumference of second extender shaft 420 and that can be tightened and loosened by rotating wheel 440 in one direction or the other, as is known in the art. Loosening and then tightening wheel 440 allows first handle 430 to be moved to a proper vertical position along the length of first extender shaft 414 as desired by the user.

a. Referring to FIG. 4, a second horizontal handle 442 surrounded by a soft material grip 444 is moveably attached to second extender shaft 446. A gripping device 448 having a gripping band 448 extending around the outer circumference of second extender shaft 420 and a tightening/loosening control wheel 448 is configured similar to gripping device 436 and allows handle 442 to also be positioned vertically along second extender shaft 420 to suit the user's needs.

b. The lower end of second extender shaft 420 includes a standing pod 450 (FIG. 4) comprising a soft flattened dome that provides stability and comfort when extender assembly 400 is being supported by a user's body part.

c. In operation of the extender assembly of the second embodiment, the handle 403 of a percussion massage device 404 is lodged in cradle 402, and flexible strap assembly 406 is extended around handle 403 until the massage device is securely held in cradle 402. The hook and loop fasteners on strap assembly 406 are brought into engagement to secure massage device 404 against movement in cradle 402.

If necessary, trigger 418 is depressed to disengage hinge assembly 416 to rotate cradle 402 until the angle between massage device 404 and extender assembly 400 desired by the user is attained. Trigger 418 is then released and hinge assembly 416 is locked in the selected position. The visual gradation indicia 419 allow the user to reposition the angular orientation between extender assembly 400 and massage device 404 to a previously preferred angular position.

I claim:

1. An extender system for a massage device handle, the extender system comprising:

a massage device including a massage device handle; and an extender comprising:

a first extender shaft extending in a first longitudinal direction;

a second extender shaft coaxial with the first extender shaft;

a cradle configured to receive the massage device, the cradle extending in a second longitudinal direction transverse to the first longitudinal direction;

a hinge assembly pivotally operable with the cradle and adjustably locking the position of the cradle relative to the first extender shaft, the hinge assembly rotatable about an axis perpendicular to the first longitudinal direction and the second longitudinal direction;

a first horizontal handle;

the first extender shaft having a first gripping device, the first gripping device configured to adjustably position the first horizontal handle about the first extender shaft, the first gripping device configured to wrap around the first extender shaft, the first extender shaft having a first end connected to the hinge assembly, and a second end adapted to receive and adjustably extend the second extender shaft; and an extension ring configured to adjustably actuate the second extender shaft out of the first extender shaft, the extension ring connecting the first extender shaft to the second extender shaft, wherein the extension ring includes a manual gripping surface and a compression fitting, wherein the manual gripping surface is configured to receive the compression fitting.

2. The extender system of claim 1, comprising:

a second horizontal handle;

the second extender shaft having a second gripping device, the second gripping device configured to adjustably position the second horizontal handle about the second extender shaft, the second extender shaft having a first end adapted to telescopically extend out from the first extender shaft, and a second end adapted to removably receive a third extender shaft or standing pod.

3. The extender system of claim 1, further including a flange extending outward from the cradle, wherein the flange is pivotally connected to the first extender shaft by the hinge assembly.

4. The extender system of claim 3, wherein the flange is a curved flange.

5. The extender system of claim 1, wherein the extension ring is configured to lock the actuated second extender shaft in place.

6. The extender system of claim 1, wherein the cradle includes two opposed slots adapted to receive a strap assembly, wherein the strap assembly is configured to secure the massage device handle to the cradle.

7. The extender system of claim 1, wherein the first extender shaft includes a connecting portion configured to connect the hinge assembly with the first extender shaft.

8. The extender system of claim 7, further including a trigger disposed on the connecting portion, the trigger pivotally operable to unlock the hinge and enable rotation of the cradle relative to the first extender shaft.

9. The extender system of claim 1, wherein the first horizontal handle extends laterally outward from the first extender shaft.

10. The extender system of claim 9, wherein the first gripping device comprises:

a gripping band configured to extend around the first extender shaft and position the first horizontal handle thereon;

a wheel mechanically attached to the first horizontal handle, wherein the wheel is configured to tighten and loosen the gripping band about the first extender shaft.

* * * * *